(12) United States Patent
Trunin et al.

(10) Patent No.: US 11,213,542 B2
(45) Date of Patent: Jan. 4, 2022

(54) METHOD AND AGENT FOR LOWERING TOTAL CHOLESTEROL LEVELS AND FOR IMPROVING BLOOD LIPID SPECTRUM COMPOSITION

(71) Applicant: Roman Anatolievich Trunin, Moscow (RU)

(72) Inventors: Roman Anatolievich Trunin, Moscow (RU); Mikhail Lvovich Uchitel, Mytishi (RU); Evgeny Ilich Maevsky, Pushino (RU)

(73) Assignee: BIOGIX, INC., El Segundo, CA (US)

( * ) Notice: Subject to any disclaimer, the term of this patent is extended or adjusted under 35 U.S.C. 154(b) by 331 days.

(21) Appl. No.: 16/329,444

(22) PCT Filed: Apr. 21, 2018

(86) PCT No.: PCT/RU2018/000278
§ 371 (c)(1),
(2) Date: Feb. 28, 2019

(87) PCT Pub. No.: WO2019/209134
PCT Pub. Date: Oct. 31, 2019

(65) Prior Publication Data
US 2021/0161940 A1    Jun. 3, 2021

(51) Int. Cl.
| | |
|---|---|
| *A61K 31/714* | (2006.01) |
| *A23L 33/175* | (2016.01) |
| *A23L 33/15* | (2016.01) |
| *A23L 33/00* | (2016.01) |
| *A61K 31/194* | (2006.01) |
| *A61K 31/198* | (2006.01) |
| *A61K 31/51* | (2006.01) |
| *A61K 31/519* | (2006.01) |
| *A61K 31/525* | (2006.01) |
| *A61K 31/555* | (2006.01) |
| *A61K 31/675* | (2006.01) |

(52) U.S. Cl.
CPC ............ *A61K 31/714* (2013.01); *A23L 33/15* (2016.08); *A23L 33/175* (2016.08); *A23L 33/40* (2016.08); *A61K 31/194* (2013.01); *A61K 31/198* (2013.01); *A61K 31/51* (2013.01); *A61K 31/519* (2013.01); *A61K 31/525* (2013.01); *A61K 31/555* (2013.01); *A61K 31/675* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2005/0238710 A1* | 10/2005 | Connolly | ............... | A61K 33/00 424/464 |
| 2005/0271754 A1* | 12/2005 | Cochrane | ............... | A61K 31/19 424/750 |
| 2006/0116334 A1* | 6/2006 | Hendrix | ................. | A61K 45/06 514/27 |
| 2015/0139972 A1* | 5/2015 | Haase | .................. | A61K 31/122 424/94.1 |
| 2016/0317554 A1* | 11/2016 | Knutsen | ................. | A61K 31/40 |

FOREIGN PATENT DOCUMENTS

| | | | | |
|---|---|---|---|---|
| CN | 104472956 A | * | 4/2015 | ............... A23K 1/18 |
| CN | 106721425 A | * | 5/2017 | ............. A23K 10/30 |
| KR | 20080094466 | * | 10/2008 | ........... A61K 31/194 |

* cited by examiner

*Primary Examiner* — Dale R Miller
(74) *Attorney, Agent, or Firm* — Bardmesser Law Group

(57) ABSTRACT

Lowering total cholesterol and improving of blood lipid spectrum composition as seen in a decrease of low and very low density lipoprotein levels, triglycerides and Lipoprotein a, and an increase in high density lipoproteins through taking fumarate and/or fumarates and B vitamins. The fumarate is any of fumaric acid, neutral or acidic sodium fumarate, potassium fumarate, ammonium fumarate, fumarate of a general formula Fum-Me-Fum.$nH_2O$, where Fum—fumaric acid anion, Me—zinc, calcium or magnesium, n=0-8 or mixture of these. The B group can be B12, B6, B2, preferably, at least two of these. Preferably also including at least one amino acid from the following: glycine, L-glutamic acid and/or its salts, L-arginine and/or its salts, L-carnitine and/or its salts, asparagine and/or its salts. Preferably also succinic, citric or isocitric acid and/or their salts. Preferably also including other vitamins, fillers, ballast substances, flavors, colors, sugars, oils.

7 Claims, No Drawings

METHOD AND AGENT FOR LOWERING TOTAL CHOLESTEROL LEVELS AND FOR IMPROVING BLOOD LIPID SPECTRUM COMPOSITION

CROSS REFERENCE TO RELATED APPLICATIONS

This application is a US National Phase of PCT/RU2018/000278, filed on Apr. 21, 2018, incorporated herein by reference in its entirety.

BACKGROUND OF THE INVENTION

Field of the Invention

The present invention relates to medicine and food industry, and, more particularly, to lowering of total cholesterol levels and improving blood lipid spectrum composition; and to an agent in the form of a dietary supplement or an over-the-counter medication for addressing these problems.

Description of the Related Art

Prevention and treatment of high cholesterol and improvement of blood lipid spectrum composition are among the top medical problems today, since the condition affects about 50% of people over the age of 60, and directly or indirectly leads to a number of illnesses.

Currently, there are several approaches to the above-mentioned problem.

First, there are dietary interventions. While these are usually sufficient during early stages of lipid metabolism dysfunctions, they are not enough to achieve significant impact for more serious cases of the condition. However, maintaining proper diet is still necessary even with the use of preventative medications.

The most effective method of lowering "bad" cholesterol is the inhibition of HMG-CoA reductase. All statin medications are based on this principle. Most frequently used are simvastatin (Vazilip, Zocor etc.), atorvastatin (Liprimar, Atoris etc.), and rosuvastatin (Crestor, Akorta etc.). First generation statins, such as pravastatin, fluvastatin, and lovastatin, are less frequently used. One of the shortcomings of this medication group is a weak effect they exert on triglycerides and lipoprotein a. In addition, there are risks of side effects negatively affecting liver and sometimes kidney functions.

Another group of drugs are derivatives of fibric acid—fibrates (Hemfibrazil, Clofibrate, Bezafibrate, Ciprofibratum, Fenofibrate); the latter (Tricor) is the most frequently used. These drugs are sufficiently effective when it comes to lowering triglycerides, but have little effect on levels of low density and very low density lipids.

The next group of drugs is cholesterol absorption inhibitors. The medications in this group are based on ezetimibe (Ezetrol). Main shortcomings of it are: high cost and low effectiveness (lower than statins).

Bile acid sequestrants (ion exchange polymers) is another group of drugs that is used. Their main advantage is that they are non-systemic drugs. Their shortcoming is somewhat low effectiveness and metabolic side effects when taken long-term.

Niacin (vitamin PP) is effective only in very high doses, which is the cause of high rates of its individual intolerance. Long-term consumption of such high doses is also potentially dangerous.

Omega-3-polyunsaturated fatty acids are sometimes used, however, they have no significant efficacy. Omega-3 is usually taken in combinations with other medications.

Metabolic regulation of lipids using high doses of vitamin PP (3-5 g one-time dose, when daily requirement is up to 20 mg) is known. Despite fast acting results and good efficacy of the method, such high doses of vitamin PP are not safe and are not well-tolerated by patients. The safe course is no more than 5 days with the impact lasting up to 2 weeks. Because of this, vitamin PP is not used in practice to treat high cholesterol.

SUMMARY OF THE INVENTION

Therefore, an object of the present invention is to provide a dietary supplement or over-the counter medicine that lowers total cholesterol levels and improves blood lipid spectrum composition, thus eliminating the disadvantages of the conventional art.

Additional features and advantages of the claimed solution are described in the following disclosure, as well as proved by the actual practice of the invention. These advantages and improvements can be achieved by neural networks that have been constructed and trained in accordance with the claimed method, specifically, following the disclosure, along with the accompanying claims and drawings.

DETAILED DESCRIPTION OF EMBODIMENTS OF THE INVENTION

Reference will now be made in detail to the embodiments of the present invention.

The proposed agents are aimed at solving a problem of metabolic regulation that allows to lower high levels of total cholesterol (TC), lower high levels of low density lipoproteins (LDL), very low density lipoproteins (VLDL), triglycerides (TG), lipoprotein a (La), while increasing levels of high density lipoproteins (HDL).

The solution to the above problem is a simultaneous administration of fumaric acid and/or compounds with fumaric acid anion and group B vitamins. This method of lipid metabolism correction was discovered by the inventors as an unexpected effect while studying combination of sodium fumarate with vitamins B1, B2, B6, B9 and B12 on stress-resistance in young and old Wistar line rats. The experiments were conducted in chronically stressed animals; a decrease of elevated levels of total cholesterol was observed in old rats.

Subsequently, the inventors conducted a detailed investigation studying the effects of the above-mentioned composition on the blood lipid spectrum and its interactions with other metabolic correctors. While the mechanism of the action remains somewhat unclear, the formulations based on the method described above lead to the normalization of lipid metabolism, having positive effects such as suppression of the total cholesterol and "bad" cholesterol, and an increase in HDL. Another important aspect of the proposed method and agent is that the metabolic changes apply to both higher than normal and lower than normal measurements. If cholesterol and its components are within normal ranges, then the proposed formulations and doses will not lead to statistically significant effects on the lipids, even with long-term administration.

Agents, based on the proposed invention, include fumarates—fumaric acid, neutral or acidic sodium fumarate, potassium fumarate, ammonium fumarate, fumarates with general formula Fum-Me-Fum.$nH_2O$, (Fum—fumaric acid anion, Me—zinc, calcium or magnesium, n=0-8) or a mixture of these fumarates and at least one vitamin from B group, preferably B6, B12 and/or B2.

To increase effectiveness of the formulation, at least one amino acid is added from the following: glycine, L-glutamic acid and/or its salts, L-arginine and/or its salts, L-carnitine and/or its salts, asparagine and/or its salts.

To increase effectiveness of the formulation, in addition to amino acids, at least one acid (or its salts) of Krebs cycle is added (besides fumaric acid or its salt), preferably amber (succinic), citric, isocitric acids and/or their salts.

The proposed agent can additionally contain other vitamins, fillers, ballast substances, flavors, colors, sugars, and/or natural oils.

The agent is mainly produced in the form of tablets, capsules, dragée, granules, powders, drinks or a set of tablets, capsules, dragée, powders and drinks.

A one-time therapeutic dose of the formulation contains 0.1-100× amount of the daily value of vitamins B and 0.1-100 mg/kg of fumaric acid anion. The formulation is to be taken for at least 5 days, and as long as needed after that.

Example 1

1.0 g of a vitamin is packed in gelatin capsules.

Example 2

1600 g of sodium fumarate is combined with 15 g of vitamin B1, 18 g of vitamin B2, 20 g of vitamin B6, 2.0 g of vitamin B9, and 0.03 g of vitamin B12. The resulting mix weighs 1655.03 g.

Example 3

1200 g of acidic sodium fumarate is combined 100 g potassium fumarate, 180 g of vitamin B2, 200 g of vitamin B6, and 1.5 g of vitamin B12. The resulting mix weighs 1681.5 g.

Example 4

920 g of acidic calcium succinate monohydrate is combined with 400 g of sodium mono-L-glutamate monohydrate, 200 g of acidic magnesium succinate tetrahydrate, 80 g of acidic zinc fumarate hydrate, 160 g of vitamin E (with E50 carrier, that contains 80 g of vitamin E), and 320 g of glycine. All of the above ingredients are thoroughly mixed; the resulting combination weighs 2080 g. The resulting mix is then combined with the 1655.03 g of mixture from example 2, totaling 3735.03 g.

Example 5

1681.5 g of the mixture from example 3 is combined with 50 g of isocitric acid, 10 g of microcrystalline cellulose, 258 g of glucose, and 0.5 g of yellow food dye. The resulting mix weighs 2000 g.

Example 6

The mixes prepared as described in examples 2-5 are then used to manufacture consumer-oriented products in various forms and by various methods. Described below are different methods of producing intermediate and final products.

The mixes are directly placed in small plastic bags; the dose per bag is specified.

Alternatively, granules are manufactured from prepared mixes as follows: two parts of the mix is combined with one part glucose and one part casein, the mix is moistened to the point of viscous flow. Capsules-dragée (0.050 g each) are then obtained from the viscous mix by spinneret (with forced air flow parallel to the spinneret's mirror).

Alternatively, tablets with specified weights are obtained directly from the mixes by using a dry press.

Alternatively, tablets with specified weight are obtained by combining two parts of the mix with one part corn starch and one part lactose. The tablets are then formed by using a dry press.

Alternatively, the mix is directly encapsulated in gelatin capsules of specified size.

Alternatively, one part of the mix is suspended in 4 parts of refined sterilized olive oil; the resulting suspension contains 20% of the formulation.

Alternatively, one part of the mix is suspended in 9 parts of distilled water, resulting in 10% mix of solution and suspension.

Example 7

Clinical trials evaluating prophylactic effects of the above-described formulations (examples 1-5) had been conducted. The studies recruited patients with abnormal levels of lipid spectrum. Different treatment courses were used for different formulations. Effectiveness was assessed by changes in total cholesterol, LDL, VLDL, HDL, TG, and La after 5, 30, 60, 90 days of supplementation, and 10 and 30 days after completing a course of treatment. Vital signs (blood pressure, pulse, ECG, general blood panel, biochemical blood panel, and urinalysis) were also monitored during the trials.

Formulation as per example 1 was used as capsules with 1000 mg of vitamin PP per capsule. Direct encapsulation was done as described in example 6.

The supplement was taken once daily, after breakfast. One-time dose (same as daily dose, see *Vitamin and mineral Requirements in human nutrition,* 2nd ed., World Health Organization 1998, incorporated herein by reference in its entirety) was 4 capsules (4000 mg of vitamin PP). The study was randomized, placebo-controlled, double-blind. The placebo group received capsules filled with corn starch that were identical in appearance and weight to the vitamin capsules. The treatment course was 5 days. The trial started with 40 patients in each group. On the second day of the trial, 2 patients dropped out from the vitamin PP group due to side effects. On the $3^{rd}$ and $4^{th}$ day of the trial, 1 and 3 patients, respectively, dropped out from the vitamin PP group also due to side effects. The trial concluded with 44 patients in the PP group and 50 patients in the placebo group (P1). The results of the study are shown in Table 1. The calculations were conducted as follows: distribution (normal or non-normal) was evaluated first, t-test was then applied to normally distributed data and Mann-Whitney to non-normally distributed data.

TABLE 1

Results of using vitamin PP to correct blood lipid spectrum

| Parameter | Group | Visit 1 Value | Visit 1 Stat. significance | Visit 2 (5 days of supplementation) Value | Visit 2 Stat. significance | Visit 3 (10 days after last dose), 15 days Value | Visit 3 Stat. significance | Visit 4 (30 days after last dose), 35 days Value | Visit 4 Stat. significance |
|---|---|---|---|---|---|---|---|---|---|
| TC, mmol/L | PP | 6.77 | no | 5.99 | ≤0.05 | 6.12 | ≤0.05 | 6.81 | no |
|  | P1 | 6.69* |  | 6.71 |  | 6.75 |  | 6.72* |  |
| HDL, mmol/L | PP | 0.98 | no | 0.99 | no | 0.95 | no | 0.99 | no |
|  | P1 | 1.04 |  | 1.02 |  | 0.98 |  | 1.00 |  |
| LDL, mmol/L | PP | 3.13 | no | 2.58 | ≤0.05 | 2.97 | no | 3.18 | no |
|  | P1 | 3.21 |  | 3.19 |  | 3.15 |  | 3.23 |  |
| VLDL, mmol/L | PP | 1.14 | no | 1.11 | no | 1.15 | no | 1.16 | no |
|  | P1 | 1.09 |  | 1.12 |  | 1.11* |  | 1.12 |  |
| TG, mmol/L | PP | 2.35* | no | 2.40 | no | 2.33 | no | 2.37 | no |
|  | P1 | 2.49 |  | 2.48 |  | 2.50 |  | 2.46 |  |
| La, mg/dL | PP | 36.75 | no | 38.39 | no | 37.40 | no | 37.29 | no |
|  | P1 | 39.14 |  | 38.68 |  | 38.86 |  | 38.91 |  |

*normal distribution

As shown in the table above, vitamin PP quickly lowers TC and LDL, without significantly changing the rest of the lipid spectrum parameters. However, vitamin PP's efficacy is limited to 10 days, and 12% of patients in the PP group dropped out due to adverse effects.

The formulation described in example 2 is made into tablets by a dry press (example 6), the resulting tablets weigh 165 g each.

One-time (daily) dose was 1 tablet after a meal (breakfast or dinner). Total administration of the supplement was 120 days. The study was a dynamic evaluation of the supplement's efficacy. Lipid spectrum and other vital signs were assessed as follows: baseline; after 30, 60, 90 and 120 days of the supplement administration; 5 days ($125^{th}$ day of the study) and 30 days ($150^{th}$ day of the study) after the last dose of the supplement. Sixty (60) patients enrolled and completed the study. The lipid spectrum parameters measured during the study are shown in Table 2.

TABLE 2

Lipid spectrum results analysis by visits

| Parameter | Visit 1, Day 0 | Visit 2, $30^{th}$ of the supplementation | Visit 3, $60^{th}$ day of supplementation | Visit 4, 90th day of supplementation | Visit 5, 120th day of supplementation | Visit 6, 5 days after last dose ($125^{th}$ day) | Visit 7, 30 days after last dose ($150^{th}$ day) |
|---|---|---|---|---|---|---|---|
| TC, mmol/L | 7.14 | 7.02 | 6.89 | 6.54 | 5.96 | 6.04 | 6.34 |
| HDL, mmol/L | 1.22 | 1.27 | 1.49 | 1.68 | 1.77 | 1.75 | 1.63 |
| LDL, mmol/L | 4.67 | 4.49 | 4.04 | 3.77 | 3.05 | 3.03 | 3.18 |
| VLDL, mmol/L | 1.27 | 1.23 | 1.09 | 0.55* | 0.33 | 0.30 | 0.35 |
| TG, mmol/L | 5.11 | 4.86 | 4.45 | 3.99 | 3.62 | 3.66 | 3.81 |
| La, mg/dL | 43.5 | 41.1 | 36.2 | 30.9 | 26.4 | 26.7 | 28.6 |

*normal distribution.

The obtained data was processed using the Friedman test. The statistical significance of the measurements is indicated in Table 3.

TABLE 3

Statistically significant changes in the lipid spectrum

| Parameter | Visit 2 vs. visit 1 | Visit 3 vs. visit 1 | Visit 4 vs. visit 1 | Visit 5 vs. visit 1 | Visit 6 vs. visit 1 | Visit 7 vs. visit 1 |
|---|---|---|---|---|---|---|
| TC, mmol/L | no | no | ≤0.10* | ≤0.05 | ≤0.05 | ≤0.05 |
| HDL, mmol/L | no | ≤0.10* | ≤0.05 | ≤0.05 | ≤0.05 | ≤0.05 |

TABLE 3-continued

Statistically significant changes in the lipid spectrum

| Parameter | Visit 2 vs. visit 1 | Visit 3 vs. visit 1 | Visit 4 vs. visit 1 | Visit 5 vs. visit 1 | Visit 6 vs. visit 1 | Visit 7 vs. visit 1 |
|---|---|---|---|---|---|---|
| LDL, mmol/L | no | no | ≤0.05 | ≤0.05 | ≤0.05 | ≤0.05 |
| VLDL, mmol/L | no | no | ≤0.05 | ≤0.05 | ≤0.05 | ≤0.05 |
| TG, mmol/L | no | no | ≤0.10* | ≤0.05 | ≤0.05 | ≤0.05 |
| La, mg/dL | no | ≤0.10* | ≤0.05 | ≤0.05 | ≤0.05 | ≤0.05 |

*trend toward statistical significance

The proposed supplement formulation exerts its effect slowly (Table 3), however, the effects last for a long time, which indirectly points to systemic changes leading to the normalization of lipid metabolism.

From 336.3 g of the mixture per example 3, 500 g of granules-dragée is prepared (per example 6). One dragée weighs 50 mg and contains 33.63 g of active ingredients.

The supplement was taken 2 times per day (morning and evening after a meal). One-time dose is 10 dragée, daily dose is 20 dragée or 672.6 mg of active ingredients.

Total course of administration was 60 days. The study was a dynamic evaluation of the supplement's efficacy. Lipid spectrum and other vital signs were assessed as follows: baseline; after 30 and 60 days of the supplement administration; 5 days ($65^{th}$ day of the study) and 30 days ($90^{th}$ day of the study) after the last dose of the supplement. Fifty (50) patients enrolled and completed the study. The lipid spectrum parameters measured during the study are shown in Table 4.

TABLE 4

Lipid spectrum results analysis by visits

| Parameter | Visit 1, Day 0 | Visit 2, $30^{th}$ day of supplementation | Visit 3, 60th day of supplementation | Visit 4, 5 days after last dose ($65^{th}$ day) | Visit 5, 30 days after last dose ($90^{th}$ day) |
|---|---|---|---|---|---|
| TC, mmol/L | 6.93 | 6.44 | 6.17 | 6.21 | 6.24 |
| HDL, mmol/L | 1.16 | 1.47 | 1.70 | 1.68 | 1.66 |
| LDL, mmol/L | 4.89 | 4.27 | 3.66* | 3.75 | 3.86 |
| VLDL, mmol/L | 1.22 | 1.01 | 0.64 | 0.66 | 0.67 |
| TG, mmol/L | 5.29 | 4.72 | 3.97 | 4.02* | 4.08 |
| La, mg/dL | 46.0 | 42.1 | 32.9 | 33.4 | 33.6 |

*normal distribution

The obtained data was processed using the Friedman test. The statistical significance of the measurements is indicated in Table 5.

TABLE 5

Statistically significant changes in the lipid spectrum

| Parameter | Visit 2 vs visit 1 | Visit 3 vs visit 1 | Visit 4 vs visit 1 | Visit 5 vs visit 1 |
|---|---|---|---|---|
| TC, mmol/L | ≤0.10* | ≤0.05 | ≤0.05 | ≤0.05 |
| HDL, mmol/L | ≤0.05 | ≤0.05 | ≤0.05 | ≤0.05 |
| LDL, mmol/L | ≤0.10* | ≤0.05 | ≤0.05 | ≤0.05 |
| VLDL, mmol/L | ≤0.10* | ≤0.05 | ≤0.05 | ≤0.05 |
| TG, mmol/L | ≤0.05 | ≤0.05 | ≤0.05 | ≤0.05 |
| La, mg/dL | ≤0.10* | ≤0.05 | ≤0.05 | ≤0.05 |

*trend toward statistical significance

Statistically significant effects become apparent after 30 days of supplementation (Table 5). The efficacy increases when the supplement is taken longer than 30 days. The effects remains (almost without diminishing) at least 30 days after the last dose of the supplement. A shortcoming of this formulation is the presence of gastrointestinal complaints (6 patients, or 12%) and exacerbation of existing chronic gastrointestinal illness (4 patients or 8%). The other formulation (per example 2) with similar composition did not result in any side effects, which is likely due to a significantly lower concentration of active ingredients.

In order to obtain high efficacy with low concentrations of active ingredients, metabolic correctors are added to the next formulation.

The formulation per example 4 is encapsulated (example 6); the resulting capsules weigh 373.5 mg each. Di-ammonium salt of amber (succinic) acid (200 mg) is added a smaller capsule of different color. The two capsules—one large and one small—make up the supplement set.

The supplement is taken once a day, after breakfast. One-time dose (same as daily dose) is 2 capsules (one large and one small). The conducted study was randomized, placebo-controlled, and double-blind. Placebo group (P2) used corn starch capsules identical in weight and appearance to the supplement capsules. The administration course was 90 days. The supplement is indicated as X4 in the results shown below. Each group enrolled 54 patients; all completed the study. The results of the trial are shown in Table 6. The calculations were done as follows: first, the mode distribution was evaluated (normal or non-normal); the normally distributed data was then analyzed using t-test, non-normally distributed data was analyzed using Mann-Whitney test.

TABLE 6 part 1 Lipid spectrum results analysis by visits

| Parameter | Group | Visit 1 Value | Visit 1 Stat. significance | Visit 2 (30 days of supplementation) Value | Visit 2 Stat. significance | Visit 3 (60 days of supplementation) Value | Visit 3 Stat. significance | Visit 4 (90 days of supplementation) Value | Visit 4 Stat. significance |
|---|---|---|---|---|---|---|---|---|---|
| TC, mmol/L | X4 | 7.23 | no | 6.59 | ≤0.05 | 6.19 | ≤0.05 | 5.91* | ≤0.05 |
| | P2 | 7.09 | | 7.16 | | 7.11 | | 7.10 | |
| HDL, mmol/L | X4 | 0.95 | no | 1.16 | no | 1.38 | ≤0.05 | 1.75 | ≤0.05 |
| | P2 | 1.01 | | 1.02 | | 1.04 | | 1.02 | |
| LDL, mmol/L | X4 | 3.26 | no | 2.67 | ≤0.05 | 2.35* | ≤0.05 | 2.19 | ≤0.05 |
| | P2 | 3.19 | | 3.22 | | 3.25 | | 3.27 | |
| VLDL, mmol/L | X4 | 1.19 | no | 0.92 | ≤0.05 | 0.76 | ≤0.05 | 0.56 | ≤0.05 |
| | P2 | 1.14 | | 1.15 | | 1.12 | | 1.12 | |
| TG, mmol/L | X4 | 5.17 | no | 4.27 | ≤0.05 | 2.67 | ≤0.05 | 2.04 | ≤0.05 |
| | P2 | 4.98 | | 4.88 | | 4.91 | | 4.93* | |
| La, mg/dL | X4 | 40.8 | no | 34.3* | ≤0.05 | 30.2 | ≤0.05 | 27.4 | ≤0.05 |
| | P2 | 39.5 | | 39.7 | | 39.4 | | 39.2 | |

TABLE 6 part 2 Lipid spectrum results analysis by visits

| Parameter | Group | Visit 5 (5 days after last dose), 95 days Value | Visit 5 Stat. significance | Visit 6 (30 days after last dose), 120 days Value | Visit 6 Stat. significance |
|---|---|---|---|---|---|
| TC, mmol/L | X4 | 5.87 | ≤0.05 | 5.92 | ≤0.05 |
| | P2 | 7.19 | | 7.14 | |
| HDL, mmol/L | X4 | 1.78 | ≤0.05 | 1.73 | ≤0.05 |
| | P2 | 1.03 | | 1.01 | |
| LDL, mmol/L | X4 | 2.24 | ≤0.05 | 2.26 | ≤0.05 |
| | P2 | 3.23 | | 3.24 | |
| VLDL, mmol/L | X4 | 0.56* | ≤0.05 | 0.56 | ≤0.05 |
| | P2 | 1.13 | | 1.13 | |
| TG, mmol/L | X4 | 2.09 | ≤0.05 | 2.10 | ≤0.05 |
| | P2 | 4.89 | | 4.95 | |
| La, mg/dL | X4 | 27.4 | ≤0.05 | 27.5 | ≤0.05 |
| | P2 | 39.8 | | 39.5 | |

*normal distribution

The obtained data was processed using the Friedman test. The statistical significance of the measurements is indicated in Table 7.

TABLE 7

Statistically significant changes in the lipid spectrum

| Parameter | Group | Visit 2 vs. visit 1 | Visit 3 vs. visit 1 | Visit 4 vs. visit 1 | Visit 5 vs. visit 1 | Visit 6 vs. visit 1 |
|---|---|---|---|---|---|---|
| TC, mmol/L | X4 | ≤0.05 | ≤0.05 | ≤0.05 | ≤0.05 | ≤0.05 |
| | P2 | no | no | no | no | no |
| HDL, mmol/L | X4 | ≤0.10* | ≤0.05 | ≤0.05 | ≤0.05 | ≤0.05 |
| | P2 | no | no | no | no | no |
| LDL, mmol/L | X4 | ≤0.05 | ≤0.05 | ≤0.05 | ≤0.05 | ≤0.05 |
| | P2 | no | no | no | no | no |
| VLDL, mmol/L | X4 | ≤0.05 | ≤0.05 | ≤0.05 | ≤0.05 | ≤0.05 |
| | P2 | no | no | no | no | no |
| TG, mmol/L | X4 | ≤0.05 | ≤0.05 | ≤0.05 | ≤0.05 | ≤0.05 |
| | P2 | no | no | no | no | no |
| La, mg/dL | X4 | ≤0.05 | ≤0.05 | ≤0.05 | ≤0.05 | ≤0.05 |
| | P2 | no | no | no | no | no |

*trend toward statistical significance

The results indicate that the above formulation is as effective as the one in example 3. No patients complained of any side effects during the course of the study. The effects of the supplement last at least 30 days after the final dose. The supplement is effective when it comes to correcting and normalizing lipid metabolism.

The mixture from example 5 is used to prepare 20% suspension in sterile olive oil (per example 6).

4 ml of the formulation (in the form of suspension) was administered once a day with a meal (lunch) to a group of 52 patients with various gastrointestinal pathologies in remission. All patients completed the study. Patients were evaluated at the baseline, on the 30th, 60th and 90th of supplementation, and 5 and 30 days after the last dose of the supplement ($95^{th}$ and $120^{th}$ day of the trial). Results of the study are shown in Table 8.

TABLE 8

Lipid spectrum results analysis by visits

| Parameter | Visit 1, day 0 | Visit 2, $30^{th}$ day of supplementation | Visit 3, 60th day of supplementation | Visit 4, 90th day of supplementation | Visit 5, 5 days after last dose ($95^{th}$ day) | Visit 6, 30 days after last dose ($120^{th}$ day) |
|---|---|---|---|---|---|---|
| TC, mmol/L | 6.94 | 6.65 | 6.37 | 6.22 | 6.24 | 6.31 |
| HDL, mmol/L | 1.03 | 1.17 | 1.39 | 1.64 | 1.65 | 1.61 |
| LDL, mmol/L | 4.88 | 4.60 | 4.21 | 4.18 | 4.25 | 4.26 |
| VLDL, mmol/L | 1.19 | 1.06 | 0.86* | 0.67 | 0.66 | 0.67 |
| TG, mmol/L | 5.36 | 4.93 | 4.54 | 4.19 | 4.19 | 4.22 |
| La, mg/dL | 40.2 | 39.0* | 37.4 | 32.1 | 33.0 | 32.8 |

*normal distribution.

The obtained data was processed using the Friedman test. The statistical significance of the measurements is indicated in Table 9.

TABLE 9

Statistically significant changes in the lipid spectrum

| Parameter | Visit 2 vs. visit 1 | Visit 3 vs. visit 1 | Visit 4 vs. visit 1 | Visit 5 vs. visit 1 | Visit 6 vs. visit 1 |
|---|---|---|---|---|---|
| TC, mmol/L | ≤0.10* | ≤0.05 | ≤0.05 | ≤0.05 | ≤0.05 |
| HDL, mmol/L | no | ≤0.05 | ≤0.05 | ≤0.05 | ≤0.05 |
| LDL, mmol/L | no | ≤0.05 | ≤0.05 | ≤0.05 | ≤0.05 |
| VLDL, mmol/L | ≤0.10* | ≤0.05 | ≤0.05 | ≤0.05 | ≤0.05 |
| TG, mmol/L | ≤0.10* | ≤0.05 | ≤0.05 | ≤0.05 | ≤0.05 |
| La, mg/dL | no | ≤0.05 | ≤0.05 | ≤0.05 | ≤0.05 |

*a trend toward statistical significance

The proposed formulation showed high efficacy; the doses were relatively high. No side effects were reported, thus, the formulation has low ulcerogenicity.

Statistically significant effects of the supplement are observed at least 30 days after the last dose.

All formulations proposed per examples 2-5 showed high efficacies when it comes to normalizing lipid metabolism in human subjects. The formulations have moderate effect, are safe, and their actions have prolonged effect.

This allows recommending the supplement with low doses of active ingredients (100-200 mg of fumaric anions and about 1 recommended daily dose of vitamin B group, per WHO recommendations, per day) for continuous prophylactic supplementation; the supplement with high doses of active ingredients (500-1000 mg of fumaric anions and about 5-10 recommended daily doses of vitamin B group, per WHO recommendations, per day) can be recommended as a therapy for lipid metabolic disorders.

Having thus described the different embodiments of the invention, it should be apparent to those skilled in the art that certain advantages of the described invention have been achieved.

What is claimed is:

1. A composition for lowering total cholesterol, triglycerides and lipoprotein A in humans, the composition comprising:
    at least one dimeric fumarate of a chelate structure; and
    at least two vitamins of the B group,
    wherein a single administration dose of the composition includes 0.1-100 daily dose of the B group vitamins, and
    wherein the dimeric fumarate in the single administration dose includes 0.1-100 mg/kg of two fumaric acid anions, and
    wherein the dimeric fumarate has a general formula Fum-Me-Fum.$nH_2O$, where Fum—fumaric acid anion, Me—zinc, calcium or magnesium, n=0-8.

2. The composition of claim 1, wherein the composition further includes any of neutral or acidic monomeric fumarates selected from sodium fumarate, potassium fumarate, ammonium fumarate or a mixture of the above.

3. The composition of claim 1, wherein the B group vitamins include vitamin B12.

4. The composition of claim 1, wherein the B group vitamins include vitamin B6.

5. The composition of claim 1, wherein the B group vitamins include vitamin B2.

6. The composition of claim 1, wherein the single administrative dose includes at least one amino acid selected from the following: glycine, L-glutamic acid and/or its salts, L-arginine and/or its salts, L-carnitine and/or its salts, asparagine and/or its salts.

7. The composition of claim 1, further comprising succinic acid, and/or citric acid, and/or isocitric acid and/or their salts.

\* \* \* \* \*